United States Patent [19]

White, Jr. et al.

[11] Patent Number: 5,096,701
[45] Date of Patent: Mar. 17, 1992

[54] ORAL COMPOSITIONS

[75] Inventors: Donald J. White, Jr., Fairfield; Edward R. Cox, Dayton; Mary A. Hunter, Cincinnati, all of Ohio

[73] Assignee: The Procter & Gamble Company, Cincinnati, Ohio

[21] Appl. No.: 629,778

[22] Filed: Dec. 18, 1990

[51] Int. Cl.$^5$ .............................. A61K 7/16; A61K 7/18
[52] U.S. Cl. .................................... 424/52; 424/49; 424/57
[58] Field of Search ..................... 424/49–58

[56] References Cited

U.S. PATENT DOCUMENTS

| | | | |
|---|---|---|---|
| 3,671,644 | 6/1972 | Irani et al. | 514/114 |
| 3,927,201 | 12/1975 | Baines et al. | 424/52 |
| 3,927,202 | 12/1975 | Harvey et al. | 424/57 |
| 3,957,967 | 5/1976 | L'Orange | 424/49 |
| 4,244,931 | 1/1981 | Jarvis et al. | 424/57 |
| 4,272,509 | 6/1981 | Wason | 424/49 |
| 4,323,551 | 4/1982 | Parran | 424/54 |
| 4,340,583 | 7/1982 | Wason | 424/52 |
| 4,350,680 | 9/1982 | Harvey et al. | 424/52 |
| 4,420,312 | 12/1983 | Wason | 424/52 |
| 4,421,527 | 12/1983 | Wason | 424/52 |
| 4,460,565 | 7/1984 | Westrate et al. | 424/52 |
| 4,515,772 | 5/1985 | Parran et al. | 424/57 |
| 4,627,977 | 12/1986 | Gaffar et al. | 424/52 |
| 4,923,684 | 5/1990 | Ibrahim et al. | 424/52 |

FOREIGN PATENT DOCUMENTS 490384 2/1937 United Kingdom .

OTHER PUBLICATIONS

Kobayashi et al., GA. 105: 139447F (1986) of Jpn 61130213, Jun. 18, 1986.
Gershon et al. GA. 115: 99028t (1991) of WO/PCT 9104008, Apr. 4, 1991.
Dobbs et al., GA. 109: 61316y (1987) of Gt. Br., 2188548, Oct. 7, 1987.
Rudy et al., GA. 105: 232227u (1986) of U.S. 4,606,912, Aug. 19, 1986.
Duke et al., GA. 103: 11248h (1985) of E.P. 137436, Apr. 17, 1985.
Duke et al., GA. 102: 100628D (1984) of E.P. 129201, Dec. 27, 1984.
Clippendale et al., GA. 73: 59318v (1970) of Ger. DE 1953944, May 6, 1970.
Pader, GA. 79: 70101p (1973) of Ger. DE 2260949, Jun. 28, 1973.
Koshimizu et al., GA. 82: 7654T (1974) of Jpn 49069848, Jul. 5, 1974.
Faunce, GA. 93: 79894w (1980) of U.S. 4,198,394, Apr. 15, 1980.
Faunce, GA. 93: 225645j (1980) of U.S. 4,203,966, May 20, 1980.

Primary Examiner—Shep K. Rose
Attorney, Agent, or Firm—Douglas C. Mohl; Kim W. Zerby; Jack D. Schaeffer

[57] ABSTRACT

Disclosed are oral compositions which are effective against calculus comprising a tripolyphosphate salt and an orthophosphate salt.

18 Claims, No Drawings

ORAL COMPOSITIONS

TECHNICAL FIELD

The present invention relates to stable oral compositions which provide an anticalculus benefit.

BACKGROUND OF THE INVENTION

Dental calculus, or tartar as it is sometimes called, is a deposit which forms on the surfaces of the teeth at the gingival margin. Supragingival calculus appears principally in the areas near the orifices of the salivary ducts; e.g., on the lingual surfaces of the lower anterior teeth and on the buccal surfaces of the upper first and second molars, and on the distal surfaces of the posterior molars.

Mature calculus consists of an inorganic portion which is largely calcium phosphate arranged in a hydroxyapatite crystal lattice structure similar to bone, enamel and dentine. An organic portion is also present and consists of desquamated epithelial cells, leukocytes, salivary sediment, food debris and various types of microorganisms.

As the mature calculus develops, it becomes visibly white or yellowish in color unless stained or discolored by some extraneous agent. In addition to being unsightly and undesirable from an aesthetic standpoint, the mature calculus deposits are regarded by some as constant sources of mechanical irritation of the gingiva.

A wide variety of chemical and biological agents have been suggested in the art to retard calculus formation or to remove calculus after it is formed. Mechanical removal of this material periodically by the dentist is, of course, routine dental office procedure.

The chemical approach to calculus inhibition generally involves chelation of calcium ion and/or crystal growth inhibition which prevents the calculus from forming and/or breaks down mature calculus by removing calcium.

The prior art discloses a number of chelating agents for this purpose. British Pat. No. 490.384. Feb. 15, 1937, discloses oral compositions containing ethylenediaminetetraacetic acid, nitrilotriacetic acid and related compounds as anticalculus agents. U.S. Pat. No. 3,678,154. July 18, 1972 to Widder et al. discloses oral compositions containing certain polyphosphonates and fluoride. U.S. Pat. No. 3,737,533, June 5, 1973 to Francis discloses oral compositions containing certain carbonyl diphosphonates.

In addition to the above references, the prior art discloses dentifrices and mouthwashes containing soluble pyrophosphate salts which have been indicated for a variety of purposes. Included among such references are U.S. Pat. No. 2,941,926, June 21, 1960 to Salzmann et al. which discloses dental powders containing chlorophyll and pyrophosphate salts. U.S. Pat. Nos. 3,927,201 and 202, Dec. 16, 1975 to Baines et al. and Harvey et al., respectively, discloses toothpastes which utilize sparingly soluble pyrophosphates as abrasives. U.S. Pat. Nos. 4,244,931, Jan. 13, 1981 and U.S. Pat. No. 4,247,526, Jan. 27, 1981 to Jarvis et al. disclose pyrophosphate salts in dicalcium phosphate systems. Japanese Patent Application Disclosure No. 4945-1974 discloses soluble pyrophosphates in a variety of dentifrice systems. U.S. Pat. No. 4,333,551, Apr. 6, 1982 to Parran discloses tetraalkali metal salts in mouthwash compositions. U.S. Pat. No. 4,515,772, May 7, 1986 to Parran et al. discloses oral compositions containing soluble pyrophosphate salts as anticalculus agents. Finally Draus, Lesniewski and Miklos, *Pyrophosphate and Hexametaphosphate Effects In Vitro Calculus Formation.* Arch. Oral Biol., Vol. 15, pp. 893–896, (1970) disclose the in vitro effectiveness of soluble pyrophosphate salts against calculus.

A reference disclosing a variety of linear molecularly dehydrated polyphosphate salts as anticalculus agents in U.S. Pat. No. 4,627,977, Dec. 9, 1986 to Gaffar et al. Included among the salts is sodium tripolyphosphate (STPP). Another reference disclosing STPP is U.S. Pat. No. 4,923,684. May 8, 1990 to Ibrahim et al. This reference discloses STPP in a toothpaste having a pH of from about 8 to about 10 to reduce the hydrolysis of the material.

The present inventors have discovered that compositions containing STPP and other alkali metal or ammonium TPP materials, while stable at pH's in the range of 9 or higher, can suffer from causing irritation problems in the mouth.

The present inventors have also discovered that compositions containing STPP at pH's of 8 and below can be stabilized against hydrolysis by the inclusion of a soluble orthophosphate compound.

It is an object, therefore, of the present invention to provide stable tripolyphosphate compositions.

It is a further object to provide compositions which provide an anticalculus benefit and an anticaries benefit.

It is still a further object of the present invention to provide an effective method for treating calculus.

These and other objects will become more clear from the detailed description which follows.

All percentages and ratios used herein are by weight of the total composition unless otherwise specified and all measurements are made at 25° C. in the composition unless otherwise specified.

SUMMARY OF THE INVENTION

The present invention embraces an oral composition comprising:
  a) an effective anticalculus amount of an alkali metal or ammonium tripolyphosphate;
  b) an effective amount of a fluoride ion source;
  c) an effective amount of a soluble orthophosphate salt; and
  d) water wherein said composition has a pH of less than about 8.0.

The present invention also encompasses a method for retarding the development of dental calculus.

By "Oral Compositions" as used herein means a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity.

By "safe and/or effective amount" as used herein means sufficient amount of material to provide the desired benefit while being safe to the hard and soft tissues of the oral cavity.

By the term "comprising", as used herein, is meant that various additional components can be conjointly employed in the compositions of this invention as long as the listed materials perform their intended functions.

By the term "carrier, as used herein, is meant a suitable vehicle which is pharmaceutically acceptable and can be used to apply the present compositions in the oral cavity.

DETAILED DESCRIPTION OF THE INVENTION

The essential as well as optional components of the present invention are described in the following paragraphs.

Tripolyphosphate Salt

The first essential component of compositions of the present invention is an alkali metal or ammonium salt of tripolyphosphate. These are commercially available materials and the preferred alkali metals are sodium and potassium with sodium being most preferred. The tripolyphosphate salt is used at a level sufficient to provide $P_3O_{10}$ ions and species at a level of about 0.5% to about 7.5%, preferably at a level of from about 2.5% to about 5.0%.

Fluoride Ion Source

The second essential component of compositions of the present invention is a fluoride ion source. The number of such sources is great and includes those disclosed in U.S. Pat. No. 3,535,421, Oct. 20, 1970 to Briner et al., incorporated herein by reference. Typical materials include:

Stannous fluoride, potassium fluoride, lithium fluoride, cesium fluoride, ammonium fluoride, aluminum fluoride, cupric fluoride, indium fluoride, stannous fluorozirconate, lead fluoride, ferric fluoride, nickel fluoride, paladium fluoride, silver fluoride, zinc fluoride, zirconium fluoride, hexylamine hydrofluoride, laurylamine hydrofluoride, myristylamine hydrofluoride, decanolamine hydrofluoride, octadecenylamine hydrofluoride, myristoxyamine, hydrofluoride, diethylaminoethyloctoylamide hydrofluoride, diethanolamineoethyloleylamide hydrofluoride, diethanolaminopropyl-N'-octadecenylamine dihydrofluoride, 1-ethanol-2-hexadecylimidazoline dihydrofluoride, octoylethanolamine hydrofluoride, octyltrimethylammonium fluoride, dodecylethyl-dimethylammonium fluoride, tetraethylammonium fluoride, dilauryl-dimethylammonium fluoride. Δ8,9-octadecenylbenzyldimethyl-ammonium fluoride, dioctyldiethylammonium fluoride, cyclohexyl-cetyldimethylammonium fluoride, furfuryllauryldimethylammonium fluoride, phenoxyethylcetyldimethylammonium fluoride, N:N'-tetramethyl-N:N;-dilauryleth-ylenediammonium difluoride, N-cetyl-pyridinium fluoride, N:N-dilauryl-morpholinium fluoride, N-myristyl-N-ethylmorpholinium fluoride, N-(octylaminocarbonylethyl)-N-benzyl-dimethylammonium fluoride, N(β-hydroxydodecyl) trimethylammonium fluoride, N-phenyl-N-hexadecyldiethylammonium fluoride, N-cyclohexyl-N-octadecyldimethylammonium fluoride, N-(2-carbomethoxyethyl)-N-benzyl-dimethylammonium fluoride, N-(2-carbocyclohexoxyethyl)-N-myristyldimethylammonium fluoride, N-(2-carbobenzyloxyethyl)-N-dodecyldimethylammonium fluoride, N-[2-(N:N'-dimethylaminocarbonyl)-ethyl]-N-dodecyldiethylammonium fluoride, N-carboxymethyl-N-cicosyldimethylammonium fluoride, betaine hydrofluoride, sarcosine stannous fluoride, alanine stannous fluoride, glycine potassium fluoride, sarcosine potassium fluoride, glycine hydrofluoride, lysine hydrofluoride, alanine hydrofluoride, betaine zirconium fluoride, sodium monofluoro phosphate and mixtures thereof. Sodium fluoride is the preferred fluoride source.

The amount of fluoride ion source can be any effective level but generally should be sufficient to provide from about 50 ppm to 3500 ppm, preferably from about 50 ppm to 1500 ppm of fluoride ions.

Ortho Phosphate Salt

The next essential component of compositions herein is a soluble orthophosphate salt. The preferred salts are those wherein the cation is an alkali metal or ammonium ion. Preferred alkali metals are sodium and potassium, with sodium being the most preferred.

The most preferred salts are monosodium phosphate, trisodium phosphate and mixtures thereof. Monosodium phosphate is also sometimes referred to as sodium acid phosphate; sodium phosphate, tribasic; sodium biphosphate; sodium orthophosphate, primary; MSP; and sodium dihydrogen phosphate. Trisodium phosphate is also sometimes referred to as TSP; sodium phosphate, monobasic; tertiary sodium phosphte; and sodium orthophosphate, tertiary.

The orthophosphate salt is present in an amount effective to provide orthophosphate anion species at levels preferably from about 0.2% to about 5.0%, more preferably from about 1.0% to about 3.0%.

Water

Water is the last essential component of compositions herein. Water employed in the preparation of commercially suitable compositions should preferably be deionized and free of organic impurities. Water generally comprises from about 10% to 50%, preferably from about 20% to 40%, by weight of the toothpaste compositions herein while mouthwashes contain from about 40% to about 95%. These amounts of water include the free water which is added plus that which is introduced with other materials as with sorbitol.

Optional Components

The compositions of the present invention may contain in addition to the above-listed components many others which will be somewhat dependent on the type of composition (mouthwashes, toothpastes, topical gels, prophylaxis pastes and the like). Toothpastes and mouthwashes are the preferred systems with toothpastes being the most preferred.

Toothpastes contain as a major component an abrasive. The abrasive polishing material contemplated for use in the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al. in U.S. Pat. No. 3,070,510. Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride and other ion sources. For these reasons they are preferred for use herein.

The silica abrasive polishing materials useful herein, as well as the other abrasives, generally have an average particle size ranging between about 0.1 and 30 microns, preferably 5 and 15 microns. The silica abrasive can be precipitated silica or silica gels such as the silica xerogels described in Pader et al., U.S. Pat. No. 3.538.230. issued Mar. 2, 1970 and DiGiulio, U.S. Pat. No. 3,862,307, June 21, 1975, both incorporated herein by reference. Preferred are the silica xerogels marketed under the tradename "Syloid" by the W.R. Grace & Company, Davison Chemical Division. Preferred precipitated silica materials include those marketed by the J.M. Huber Corporation under the tradename, "Zeodent", particularly the silica carrying the designation "Zeodent 119". These silica abrasive are described in U.S. Pat. No. 4.340.583. July 29, 1982, incorporated herein by reference.

The abrasive in the toothpaste compositions described herein is present at a level of from about 6% to about 70%, preferably from about 15% to about 30%.

Flavoring agents can also be added to the dentifrice and other compositions of the present invention. Suitable flavoring agents include oil of wintergreen, oil of peppermint, oil of spearmint, oil of sassafras, and oil of clove. Sweetening agents are also useful and include aspartame, acesulfame, saccharin, dextrose, levulose and sodium cyclamate. Flavoring and sweetening agents are generally used in the compositions herein at levels of from about 0.005% to about 2% by weight and may be used as a solvent for the antibacterials hereinbefore indicated.

In preparing toothpastes, it is necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth and polysaccharide gums such as xanthan gum can also be used. Colloidal magnesium aluminum silicate or finely divided silica can be used as part of the thickening agent to further improve texture. Thickening agents in an amount from 0.1% to 5.0% by weight of the total composition, preferably from about 0.5% to about 4.0%, may be used.

It is also desirable to include a humectant in a toothpaste to keep it from hardening. Suitable humectants include glycerin, sorbitol, and other edible polyhydric alcohols at a level of from about 10% to about 70%.

Still another optional component for use in the compositions of the present invention is an additional anticalculus agent. These agents include any which are effective against calculus such as pyrophosphate salts as disclosed in U.S. Pat. No. 4,515,772. May 7, 1985 incorporated herein by reference. The preferred agents are mono, di, tri and tetra alkali metal and ammonium pyrophosphate. Such agents are used in amounts sufficient to reduce calculus. These amounts are preferably in an amount of at least about 1% $P_2O_7$, most preferably at least about 1.3%, most preferably at least about 1.5%.

Surfactants are also useful in the compositions of this invention include many different materials. Suitable surfactants include any which are reasonably stable and function over a wide pH range. Included are non-soap anionic, nonionic, cationic, zwitterionic and amphoteric organic synthetic surfactants. Many of these are disclosed by Gieseke et al. in U.S. Pat. No. 4,051,234, Sept. 27, 1988 incorporated herein in total by reference.

Preferred surfactants include alkyl sulfates, particularly Na or $NH_4$ alkyl $C_{12}$-$C_{14}$ sulfate. Any surfactant used is at a level of from about 0.2% to about 7.0%, preferably from about 0.6% to about 7%.

Polyethylene glycols are also useful in this invention can be any of a wide range of molecular weights such as from about 100 to about 1,000, preferably from about 300 to about 600. The glycol is present in an amount of from about 1% to about 10%, preferably from about 3% to about 6%.

Another optional component for use in compositions of this invention is a water insoluble, noncationic antibacterial. Suitable agents are those described in G.B. 2,200,551. Aug. 10, 1988 incorporated herein by reference. A preferred material is triclosan (2:4,4'-trichloro-2-hydroxy-diphenyl ether). This type of antibacterial is used at a level of from about 0.1% to about 5%, preferably from about 0.03% to about 1%.

Other useful components of the compositions of this invention are anionic polymeric polycarboxylates. Such materials are well known, being employed in the form of their free acids or partially or preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez (AN 139(M.W. 500,000), A.N. 119 (M.W. 250,000) and preferably S-97 Pharmaceutical Grade (M.W. 70,000), of GAF Corporation.

Other operative polymeric polycarboxylates include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates disclosed in above referred to U.S. Pat. Nos. 4,138,477 and 4,183,914, incorporated herein by reference, include copolymers of maleic anhydride with styrene, isobutylene or ethyl vinyl ether, polyacrylic, polyitaconic and polymaleic acids, and sulfoacrylic oligomers of M.W. as low as 1,000 available as Uniroyal ND-2.

Suitable generally are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

The linear anionic polymeric polycarboxylate component is mainly a hydrocarbon with optional halogen and O-containing substituents and linkages as present in for example ester, ether and OH groups, and when present is generally employed in the instant compositions in approximate weight amounts of 0.05 to 3%, preferably 0.05 to 2%, more preferably 0.1 to 2%.

Another preferred embodiment of the present invention is a mouthwash composition. Mouthwashes generally comprise from about 20:1 to about 2:1 of a water-/ethyl alcohol solution and preferably other ingredients such as flavor, sweeteners, humectants and sudsing agents such as those described above. The humectants, such as glycerin and sorbitol give a moist feel to the mouth. Generally, on a weight basis the mouthwashes of the invention comprise 5% to 60% (preferably 10% to 25%) ethyl alcohol, 0% to 20% (preferably 5% to 20%) of a humectant, 0% to 2% (preferably 0.01% to 0.15%) emulsifying agent, 0% to 0.5% (preferably 0.005% to 0.06%) sweetening agent such as saccharin, 0% to 0.3% (preferably from 0.03% to 0.3%) flavoring agent, and the balance water.

The pH of the present compositions and/or its pH in the mouth can be any pH which is safe for the mouth's hard and soft tissues. Such pH's are generally from about 3 to about 10, preferably from about 4 to about 9.

| Material | Weight % |
|---|---|
| Water | 24.129 |
| Sorbitol | 26.200 |
| NaF | 0.243 |
| Saccharin | 0.460 |
| Trisodium Phosphate | 3.130 |
| Monosodium Phosphate | 0.868 |
| PEG 6 | 3.000 |
| TiO$_2$ | 0.500 |
| FD&C Blue #1 | 0.050 |
| Sodium Tripolyphosphate | 4.520 |
| Silica | 22.000 |
| Glycerin | 9.000 |
| Xanthan Gum | 0.600 |
| Carbopol ® 956* | 0.200 |
| Flavor | 1.100 |
| SASS | 4.000 |

*Carboxyvinyl polmer offered by B. F. Goodrich Co.

| Material | Weight % |
|---|---|
| Glycerin | 10.00 |
| Ethanol | 10.00 |
| Pluronic F108 | 3.80 |
| Na Saccharin | 0.03 |
| Trisodium Phosphate | 1.04 |
| Monosodium Phosphate | 0.29 |
| Sodium Tripolyphosphate | 1.51 |
| Flavor | 0.22 |
| NaOH/HCl & Water to 100.00 | pH 7.50 |

What is claimed:

1. An oral composition consisting essentially of
   a) an amount of a water soluble tripolyphosphate salt sufficient to provide from about 0.5% to about 7.5% of P$_3$O$_{10}$ ions and species;
   b) an amount of a water soluble fluoride ion source sufficient to provide from about 50 ppm to about 1500 ppm of fluoride ions;
   (c) an amount of a water soluble monosodium and/or trisodium orthophosphate salt sufficient to provide from about 0.2% to about 5.0% of orthophosphate anion species; and
   d) water.

2. A composition according to claim 1 wherein said tripolyphosphate salt and ortho phosphate salt are sodium salts.

3. A composition according to claim 2 wherein the fluoride ion source is sodium fluoride.

4. A composition according to claim 3 wherein said composition is a toothpaste or a mouthwash.

5. A composition according to claim 4 wherein said composition is a toothpaste which in addition contains an abrasive and a binder.

6. A composition according to claim 5 wherein said toothpaste additionally contains a wear insoluble, noncationic anti-bacterial agent.

7. A composition according to claim 6 wherein said antibacterial agent is trichlosan.

8. A composition according to claim 4 wherein the composition is a mouthwash and in addition contains a humectant.

9. A composition according to claim 8 wherein the orthophosphate and tripolyphosphate salts are sodium salts.

10. A composition according to claim 9 which in addition contains an additional anticalculus agent.

11. A composition according to claim 10 which in addition contains a water-insoluble, noncationic antibacterial agent.

12. A composition according to claim 11 wherein said antibacterial agent is triclosan.

13. A process for reducing calculus of those susceptible to forming calculus and for treating diseases of the oral cavity by applying to said cavity an effective amount of a composition according to claim 1.

14. A process for treating diseases of the oral cavity by applying to said cavity an effective amount of a composition made according to claim 2.

15. A process for treating diseases of the oral cavity by applying to said cavity an effective amount of a composition according to claim 5.

16. A process for treating diseases of the oral cavity by applying to said cavity an effective amount of a composition according to claim 6.

17. A process for treating diseases of the oral cavity by applying to said cavity an effective amount of a composition made according to claim 8.

18. A process for treating diseases of the oral cavity by applying to said cavity an effective amount of a composition made according to claim 11.

* * * * *